United States Patent [19]

Ohsaka et al.

[11] Patent Number: 4,709,060
[45] Date of Patent: Nov. 24, 1987

[54] SUBSTITUTED TRIFLUOROOXETANES

[75] Inventors: Yohnosuke Ohsaka, Ibaraki; Shoji Takaki, Toyonaka, both of Japan

[73] Assignee: Daikin Industries, Ltd., Osaka, Japan

[21] Appl. No.: 884,507

[22] Filed: Jul. 11, 1986

Related U.S. Application Data

[63] Continuation-in-part of Ser. No. 691,894, Jan. 16, 1985, abandoned.

[30] Foreign Application Priority Data

Jan. 20, 1984 [JP] Japan .................................. 59-8768

[51] Int. Cl.$^4$ ............................................. C07D 305/08
[52] U.S. Cl. ...................................... 549/511; 568/674
[58] Field of Search .......................................... 549/551

[56] References Cited

U.S. PATENT DOCUMENTS

| | | | |
|---|---|---|---|
| 2,995,571 | 8/1961 | Harris | 549/511 |
| 2,995,572 | 8/1961 | Harris | 549/511 |
| 3,114,778 | 12/1963 | Fritz et al. | 568/674 |
| 3,125,581 | 3/1964 | Coffman et al. | 549/511 |
| 3,164,610 | 1/1965 | Davis | 549/511 |
| 3,417,102 | 12/1968 | Braun | 549/511 |

Primary Examiner—Norma S. Milestone
Attorney, Agent, or Firm—Birch, Stewart, Kolasch and Birch

[57] ABSTRACT

A substituted trifluorooxetane of the formula:

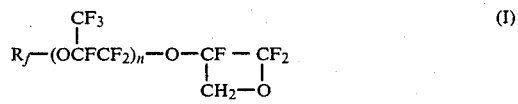

or

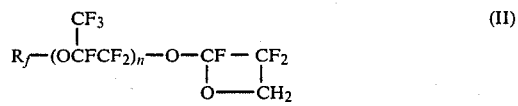

wherein $R_f$ is a $C_1$–$C_{10}$ perfluoroalkyl group and n is 0, 1 or 2, which is useful as a solvent or a monomer.

4 Claims, No Drawings

SUBSTITUTED TRIFLUOROOXETANES

This application is a continuation-in-part of application Ser. No. 691,894, filed Jan. 16, 1985, now abandoned.

FIELD OF THE INVENTION

The present invention relates to a novel substituted trifluorooxetane and preparation thereof.

DETAILED DESCRIPTION OF THE INVENTION

The novel substituted trifluorooxetane of the invention is a cyclic compound of the formula:

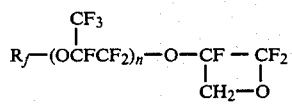

(I)

or

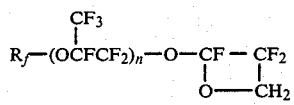

(II)

wherein $R_f$ is a $C_1$–$C_{10}$ perfluoroalkyl group and n is 0, 1 or 2.

Perfluoroalkoxytrifluorooxetane (I) or (II) is per se useful as a solvent or a monomer which is ring opened to produce an oligomer or a polymer. The oligomer or polymer of the substituted trifluorooxetane (I) or (II) finds the same application as conventional fluororesins and perfluoropolyethers.

The substituted trifluorooxetane (I) and (II) may be prepared by reacting a perfluoroether of the formula:

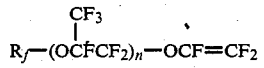

(III)

wherein $R_f$ and n are the same as defined above with paraformaldehyde in the presence of hydrogen fluoride.

The perfluoroether (III) wherein n is 0 is prepared by a method described in U.S. Pat. No. 3,114,778 and the perfluoroether (III) wherein n is 1 or 2 is prepared by reacting hexafluoropropyleneoxide with a corresponding acid fluoride of the formula:

(IV)

wherein $R_f$ is the same as defined above to obtain a compound of the formula:

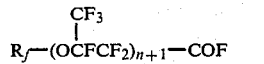

(V)

and then thermally decomposing the compound (V).

A molar ratio of the perfluoroether (III) and paraformaldehyde is usually from 1:0.5 to 1:3, preferably from 1:0.7 to 1:1.5. Hydrogen fluoride is present in the reaction system in an amount of 3 to 20 moles, preferably 5 to 10 moles per mole of paraformaldehyde. A reaction temperature is usually from 50° to 150° C., preferably from 80° to 120° C. Preferably, the reaction is carried out in a liquid phase. The produced substituted trifluorooxetane may be recovered from the reaction mixture by a per se conventional method, for example, by distilation.

The present invention will be hereinafter explained further in detail by following Examples.

REFERENCE EXAMPLE 1

Preparation of $CF_2O$ $CF_2O$ is prepared by the method described by Molis Hudlicky in Chemistry of Organic Fluorine Compounds, 2nd Ed., (1976) 678, Ellis Horwood Limited.

REFERENCE EXAMPLE 2

Preparation of $CF_3CF_2COF$ $CF_3CF_2COF$ (b.p. −28° C.) is prepared by flowing hexafluoropropylene oxide through a stainless steel reactor tube containing active carbon carrying 3% by weight of potassium fluoride kept at 150° C.

REFERENCE EXAMPLE 3

Preparation of $C_9F_{19}COF$

According to the method described by Hazeldine et al in J. Chem. Soc., 1953, 3761, $C_{10}F_{21}I$ (b.p. 102°–6° C./45 mmHg) is prepared and then reacted with fuming sulfuric acid at 150° C. for 6 hours to obtain $C_9F_{19}COF$ (b.p. 124°–5° C.).

REFERENCE EXAMPLE 4

Preparation of $CF_3(OCF(CF_3)CF_2)_2OCF=CF_2$ (a) To a stainless steel 300 ml autoclave, diglyme (100 ml) and cesium fluoride (0.2 g) were added and cooled to −20° C. followed by evacuation. After adding $CF_2O$ (5 g), hexafluoropropylene oxide (14 g) was added over one hour and then reacted for 4 hours. The reaction mixture was distilled to recover $CF_3(OCF(CF_3)CF_2)_2OCF(CF_3)COF$ (7 g) at 128°–30° C.

(b) After pH of the acid fluoride obtained in the above step (a) was adjusted to 10 with a 10% by weight aqueous solution of potassium hydroxide, the obtained potassium salt was dried at 80° C. and heated at 180° C. to obtain $CF_3(OCF(CF_3)CF_2)_2OCF=CF_2$ (4 g). b.p. 110°–3° C.

REFERENCE EXAMPLE 5

Preparation of $CF_3OCF=CF_2$ (a) To a stainless steel 300 ml autoclave, diglyme (100 ml) and cesium fluoride (0.2 g) was added and cooled to −10° C. followed by evacuation. After adding $CF_3CF_2COF$ (10 g), hexafluoropropylene oxide (10 g) was added over one hour and then reacted for another one hour. The reaction mixture was distilled to recover $C_3F_7OCF(CF_3)COF$ (16 g) at 56° C.

(b) After pH of the acid fluoride obtained in the above step (a) was adjusted to 10 with a 10% by weight aqueous solution of potassium hydroxide, the obtained potassium salt was dried at 80° C. and heated at 250° C. to obtain $C_3F_7OCF=CF_2$ (9 g). b.p. 56° C.

REFERENCE EXAMPLE 6

Preparation of $C_3F_7OCF(CF_3)CF_2OCF=CF_2$ (a) In the same manner as in Reference Example 5 (a) but using 20 g of hexafluoropropylene oxide and carrying out the reaction at −20° C., the reaction was proceeded to obtain $C_3F_7OCF(CF_3)CF_2OCF(CF_3)COF$ (9 g). b.p. 114°–6° C.

(b) In the same manner as in Reference Example 5 (b) but heating at 200° C., the reaction was proceeded to obtain $C_3F_7OCF(CF_3)CF_2OCF=CF_2$ (4 g). b.p. 98°–100° C.

REFERENCE EXAMPLE 7

Preparation of $C_{10}F_{21}OCF(CF_3)CF_2OCF=CF_2$ (a) To a stainless steel 300 ml autoclave, diglyme (100 ml) and cesium fluoride (0.2 g) was added and cooled to −10° C. followed by evacuation. After adding $C_9F_{19}COF$ (10 g), hexafluoropropylene oxide (6.4 g) was added over one hour and then reacted for 3 hours. The reaction mixture was distilled to recover $C_{10}F_{21}OCF(CF_3)CF_2OCF(CF_3)COF$ (11 g) at 112°–5° C./50 mmHg.

(b) After pH of the acid fluoride obtained in the above step (a) was adjusted to 10 with a 10% by weight aqueous solution of potassium hydroxide, the obtained potassium salt was dried at 80° C. and heated at 150° C. to obtain $C_{10}F_{21}OCF(CF_3)CF_2OCF=CF_2$ (6 g). b.p. 89°–90° C.

EXAMPLE 1

To a 3 liter stainless steel made autoclave, perfluoro(propyl vinyl ether) (800 g), paraformaldehyde (180 g) and anhydrous hydrogen fluoride (1,400 g) were charged and reacted with stirring at 80° C. for 15 hours.

Thereafter, the reaction mixture was gradually poured into ice-cold water and thoroughly stirred. Then, the organic layer was recovered by liquid-liquid separation, washed with water and treated with soda lime to obtain an organic mixture (680 g), which was distilled under reduced pressure to give a distillate (185 g) containing a compound of the formula:

$$C_3F_7O-CF-CF_2 \atop |\quad\quad| \atop CH_2-O \quad\quad\quad (Ia)$$

and a compound of the formula:

$$C_3F_7O-CF-CF_2 \atop |\quad\quad| \atop O\quad\quad CH_2 \quad\quad\quad (IIa)$$

in a molar ratio of about 61:39.

Analysis of the compound (Ia)

MS: m/e=236 (M-30), 169 ($C_3F_7$).

$^1$H-NMR (in acetone-d$_6$): 4.4 ppm (d).

$^{19}$F-NMR (standard: trifluoroacetic acid): 5.5 ppm (t, $CF_3-CF_2-$), 52.9 ppm (m, $CF_3-CF_2-$), 7.2 ppm (t, $-CF_2-CF_2-O-$), 10.8 (m,

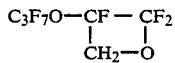

2.2 ppm (m,

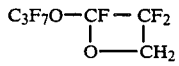

Analysis of the compound (IIa)

MS: m/e=236 (M-30), 169 ($C_3F_7$).

$^1$H-NMR (in acetone-d$_6$): 4.8 ppm (d).

$^{19}$F-NMR (standard: trifluoroacetic acid): 5.5 ppm (t, $CF_3-CF_2-$), 52.9 ppm (m, $CF_3-CF_2-$), 7.2 ppm (t, $-CF_2-CF_2-O-$), 10.2 (m,

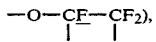

42 ppm (m,

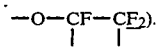

EXAMPLE 2

To a 100 ml stainless steel made reactor, perfluoro(propyl vinyl ether) (26.6 g), paraformaldehyde (6.0 g) and anhydrous hydrogen fluoride (50 g) were charged and reacted with stirring at 110° C. for 12 hours.

Thereafter, the reaction mixture was poured into ice-cold water and stirred. Then, the organic layer was recovered by liquid-liquid separation, washed with water and treated with soda lime to obtain an organic mixture (17.4 g), which was distilled under reduced pressure to give a distillate containing 15.8% by mole of the compound (Ia) and 9.0% by mole of the compound (IIa).

EXAMPLE 3

To a 100 ml stainless steel made autoclave, perfluoro(propyl vinyl ether) (26.6 g), paraformaldehyde (3.0 g) and anhydrous hydrogen fluoride (30 g) were charged and reacted with stirring at 50° C. for 24 hours.

Thereafter, the reaction mixture was treated in the same manner as in Example 1 to obtain a reaction product mixture (22.0 g), which contained 3.0% by mole of the compound (Ia) and 1.7% by mole of the compound (IIa).

EXAMPLE 4

To a 100 ml stainless steel made autoclave, a compound (30.0 g) of the formula:

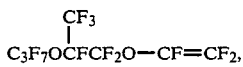

paraformaldehyde (6.0 g) and anhydrous hydrogen fluoride (50 g) were charged and reacted with stirring at 100° C. for 5 hours.

Thereafter, the reaction mixture was treated in the same manner as in Example 1 to obtain a reaction product mixture (18.8 g), which was distilled in vacuo to give a distillate (3.0 g) containing a compound of the formula:

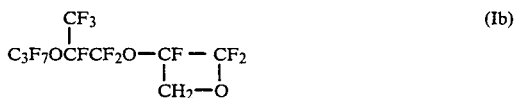

and a compound of the formula:

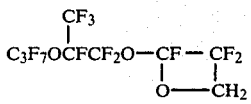 (IIb)

in a molar ratio of about 6:4.

Analysis of the compound (Ib)

MS: m/e=432 (M-30), 169 ($C_3F_7$), 69 ($CF_3$).

$^1$H-NMR (in acetone-$d_6$): 4.4 ppm (d).

$^{19}$F-NMR (standard: trifluoroacetic acid): 5.5 ppm (t, $CF_3$—$CF_2$—), 52.9 ppm (m, $CF_3$—$CF_2$—$CF_2$—), 7.2 ppm (t, —$CF_2$—$CF_2$—O—), 68 ppm (m,

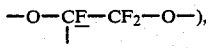

3.8 ppm (m, —$CF(CF_3)$—$CF_2$—), 2.2 ppm (m, —$CF(CF_3)$—$CF_2$—O—), 10.6 ppm (m,

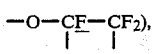

2.0 ppm (m,

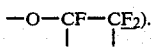

Analysis of the compound (IIb)

MS: m/e=432 (M-30), 169 ($C_3F_7$), 69 ($CF_3$).

$^1$H-NMR (in acetone-$d_6$): 4.8 ppm (d).

$^{19}$F-NMR (standard: trifluoroacetic acid): 5.5 ppm (t, $CF_3$—$CF_2$—), 52.9 ppm (m, $CF_3$—$CF_2$—$CF_2$—), 7.2 ppm (t, —$CF_2$—$CF_2$—O—), 68 ppm (m,

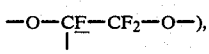

3.8 ppm (m, —$CF(CF_3)$—$CF_2$—), 2.2 ppm (m, —$CF(CF_3)$—$CF_2$—O—), 10 ppm (m,

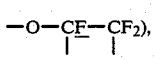

42 ppm (m,

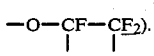

EXAMPLE 5

To a 100 ml stainless steel made autoclave, perfluoro(butyl vinyl ether) (25.0 g), parafluoromaldehyde (5.0 g) and anhydrous hydrogen fluoride (50 g) were charged and reacted with stirring at 80° C. for 20 hours.

Thereafter, the reaction mixture was treated in the same manner as in Example 1 to obtain a reaction product mixture (22.0 g), which was distilled in vacuo to give a distillate (4.5 g) containing a compound of the formula:

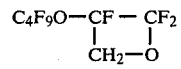 (Ic)

and a compound of the formula:

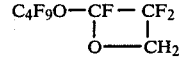 (IIc)

in a molar ratio of about 6:4.

The structures of the compounds were determined by the same methods as in Example 1.

EXAMPLE 6

To a 100 ml stainless steel made autoclave, a perfluoroether (0.04 mol) of the formula:

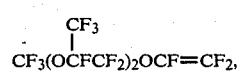

paraformaldehyde (2.4 g) and anhydrous hydrogen fluoride (20 g) were charged and reacted with stirring at 100° C. for 10 hours.

Thereafter, the reaction mixture was treated in the same manner as in Example 1 to obtain a reaction product mixture, which was distilled in vacuo to give a distillate (2.1 g) containing a compound of the formula:

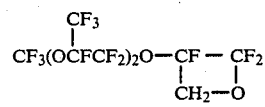 (Id)

and a compound of the formula:

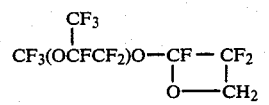 (IId)

in a molar ratio of about 65:35 (determined from signal strength of $^1$H-NMR).

Analysis of the compound (Id)

MS: m/e=498 (M-30), 69 ($CF_3$).

$^1$H-NMR (in acetone-$d_6$): 4.4 ppm (d).

$^{19}$F-NMR (standard: trifluoroacetic acid):-10 ppm (t,

68 ppm (m, —$CF(CF_3)$—$CF_2$—), 3.8 ppm (m, —$CF(CF_3)$—$CF_2$—), 2.2 ppm (m, —$CF(CF_3)$—$CF_2$—), 10.6 ppm (m,

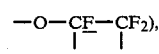

2.0 ppm (m,

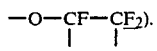

Analysis of the compound (IId)

MS: m/e=498 (M-30), 69 (CF$_3$).

$^1$H-NMR (in acetone-d$_6$): 4.8 ppm (d).

$^{19}$F-NMR (standard: trifluoroacetic acid): 10 ppm (t,

68 ppm (m, —CF(CF$_3$)—CF$_2$—), 3.8 ppm (m, —CF(CF$_3$)—CF$_2$—), 2.2 ppm (m, —CF(CF$_3$)—CF$_2$—), 9.8 ppm (m,

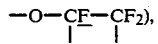

42 ppm (m,

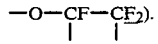

EXAMPLE 7

To a 100 ml stainless steel made autoclave, a perfluoroether (0.05 mol) of the formula:

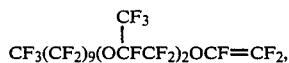

paraformaldehyde (3.1 g) and anhydrous hydrogen fluoride (20 g) were charged and reacted with stirring at 120° C. for 10 hours.

Thereafter, the reaction mixture was treated in the same manner as in Example 1 to obtain a reaction product mixture, which was distilled in vacuo to give a distillate (5.2 g) containing a compound of the formula:

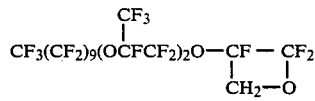

and a compound of the formula:

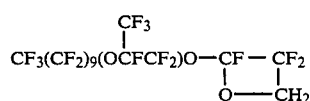

in a molar ratio of about 55:45.

Analysis of the compound (Ie)

MS: m/e=752 (M-30), 519 (C$_{10}$F$_{21}$), 169 (C$_3$F$_7$), 69 (CF$_3$).

$^1$H-NMR (in acetone-d$_6$): 4.4 ppm (d).

$^{19}$F-NMR (standard: trifluoroacetic acid): 4.9 ppm (t, CF$_3$—CF$_2$—), 51 ppm (br, CF$_3$—CF$_2$—), 48 ppm (m, CF$_3$CF$_2$—(CF$_2$)$_7$—CF$_2$—), 7.0 ppm (m, CF$_3$CF$_2$—(CF$_2$)$_7$—CF$_2$—), 67 ppm (m, —O—CF(CF$_3$)—CF$_2$—), 3.8 ppm (m, —CF(CF$_3$)—CF$_2$—), 2.2 ppm (m, —CF(CF$_3$)—CF$_2$—O—), 58 ppm (m,

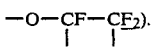

2.0 ppm (m,

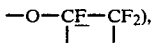

Analysis of the compound (IIe)

MS: m/e=752 (M-30), 519 (C$_{10}$F$_{21}$), 169 (C$_3$F$_7$), 69 (CF$_3$).

$^1$H-NMR (in acetone-d$_6$): 4.8 ppm (d).

$^{19}$F-NMR (standard: trifluoroacetic acid): 4.9 ppm (t, CF$_3$—CF$_2$—), 51 ppm (br, CF$_3$—CF$_2$—), 48 ppm (m, CF$_3$CF$_2$—(CF$_2$)$_7$—CF$_2$—), 7.0 ppm (m, CF$_3$CF$_2$—(CF$_2$)$_7$—CF$_2$—), 67 ppm (m, —O—CF(CF$_3$)—CF$_2$—), 3.8 ppm (m, —CF(CF$_3$)—CF$_2$—), 2.2 ppm (m, —CF(CF$_3$)—CF$_2$—O—), 10 ppm (m,

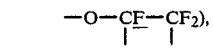

420 ppm (m,

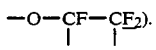

What is claimed is:

1. A substituted trifluorooxetane of the formula:

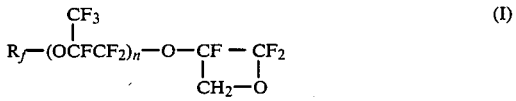

or

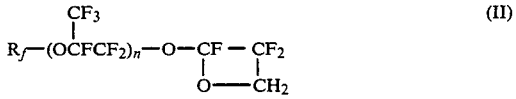

wherein R$_f$ is a C$_1$–C$_{10}$ perfluoroalkyl group and n is 0, 1 or 2.

2. The substituted trifluorooxetane according to claim 1, wherein n is 0 (zero).

3. The substituted trifluorooxetane according to claim 1, wherein n is 0 and R$_f$ is perfluoropropyl or perfluorobutyl.

4. The substituted trifluorooxetane according to claim 1, wherein n is 1 or 2.

* * * * *